United States Patent [19]
Myers et al.

[11] Patent Number: 5,147,297
[45] Date of Patent: Sep. 15, 1992

[54] IONTOPHORETIC DELIVERY DEVICE

[75] Inventors: Robert M. Myers, Stanford; Mark G. Stahl, Sunnyvale, both of Calif.

[73] Assignee: Alza Corporation, Palo Alto, Calif.

[21] Appl. No.: 521,761

[22] Filed: May 7, 1990

[51] Int. Cl.$^5$ ............................................... A61N 1/30
[52] U.S. Cl. ..................................... 604/20; 128/798
[58] Field of Search ................. 604/20; 128/798, 802, 128/803, 898

[56] References Cited

U.S. PATENT DOCUMENTS

| | | | |
|---|---|---|---|
| 3,976,055 | 8/1976 | Monter et al. | 128/2.06 |
| 3,991,755 | 11/1976 | Vernon et al. | 128/172 |
| 4,141,359 | 2/1979 | Jacobsen et al. | 128/172.1 |
| 4,250,878 | 2/1981 | Jacobsen et al. | 128/207.21 |
| 4,367,745 | 1/1983 | Welage | 128/303.13 |
| 4,383,529 | 5/1983 | Webster | 604/20 |
| 4,398,545 | 8/1983 | Wilson | 128/798 |
| 4,474,570 | 10/1984 | Ariura et al. | 604/20 |
| 4,640,689 | 2/1987 | Sibalis | 604/20 |
| 4,731,049 | 3/1988 | Parsi | 604/20 |
| 4,744,787 | 5/1988 | Phipps et al. | 604/20 |
| 4,747,819 | 5/1988 | Phipps et al. | 604/20 |
| 4,752,285 | 6/1988 | Petelenz et al. | 604/20 |
| 4,764,164 | 8/1988 | Sasaki | 604/20 |
| 4,842,577 | 6/1989 | Konno et al. | 604/20 |
| 4,927,408 | 5/1990 | Haak et al. | 604/20 |
| 4,940,456 | 7/1990 | Sibalis et al. | 604/20 |
| 5,087,242 | 2/1992 | Petelenz et al. | 604/20 |

OTHER PUBLICATIONS

CRC Handbook of Chemistry & Physics, 57th Ed., (1976-1977) pp. D141-146, "Electrochemical Series", Table I, compiled by J. F. Hunsberger.
CRC Handbook of Chemistry & Physics, 67th Ed., (1986-1987), pp. D151-158, "Electrochemical Series," Table I, by Petr Vanysek Dorland's Pocket Medical Dictionary, 23rd Ed., p. 362.

Primary Examiner—Stephen C. Pellegrino
Assistant Examiner—Michael Rafa
Attorney, Agent, or Firm—D. Byron Miller; Edward L. Mandell; Steven F. Stone

[57] ABSTRACT

An electrically powered iontophoretic delivery device is provided. The device utilizes electrodes composed of a polymeric matrix containing about 5 to 40 vol % of a conductive filler which forms a conductive network through the matrix, and about 5 to 40 vol % of a chemical species which is able to undergo either oxidation or reduction during operation of the device. Preferably, the conductive filler is carbon or graphite fibers. For the anode electrode, the chemical species should be able to undergo oxidation and is preferably either silver or zinc. For the cathode electrode, the chemical species should be able to undergo reduction and is preferably silver chloride.

46 Claims, 1 Drawing Sheet

IONTOPHORETIC DELIVERY DEVICE

TECHNICAL FIELD

This invention relates to a device for delivering an agent transdermally or transmucosally by iontophoresis. More particularly, this invention relates to an electrically powered iontophoretic delivery device having a polymer-based electrode.

BACKGROUND ART

Iontophoresis, according to Dorland's Illustrated Medical Dictionary, is defined to be "the introduction, by means of electric current, of ions of soluble salts into the tissues of the body for therapeutic purposes." Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming a galvanic cell from the electrodes and the material containing the medicament or drug to be delivered transdermally. The galvanic cell produced the current necessary for iontophoretically delivering the medicament. This ambulatory device thus permitted iontophoretic drug delivery with substantially less interference with the patient's daily activities.

More recently, a number of United States patents have issued in the iontophoresis field, indicating a renewed interest in this mode of drug delivery. For example, U.S. Pat. No. 3,991,755 issued to Vernon et al; U.S. Pat. No. 4,141,359 issued to Jacobsen et al; U.S. Pat. No. 4,398,545 issued to Wilson; and U.S. Pat. No. 4,250,878 issued to Jacobsen disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate, insulin and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

In presently known iontophoretic devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged (i.e., a cation), then the anode will be the active electrode and the cathode will serve to complete the circuit. If the ionic substance to be delivered is negatively charged (i.e., an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

It is also known that iontophoretic delivery devices can be used to deliver an uncharged drug or agent into the body. This is accomplished by a process called electroosmosis. Electroosmosis is the transdermal flux of a liquid solvent (e.g., the liquid solvent containing the uncharged drug or agent) which is induced by the presence of an electric field imposed across the skin by the donor electrode.

Furthermore, existing iontophoresis devices generally require a reservoir or source of the beneficial agent (which is preferably an ionized or ionizable agent or a precursor of such agent) to be iontophoretically delivered into the body. Examples of such reservoirs or sources of ionized or ionizable agents include a pouch as described in the previously mentioned Jacobsen U.S. Pat. No. 4,250,878, or a pre-formed gel body as described in Webster U.S. Pat. No. 4,383,529 and Ariura et al. U.S. Pat. No. 4,474,570. Such drug reservoirs are electrically connected to the anode or the cathode of an iontophoresis device to provide a fixed or renewable source of one or more desired agents.

More recently, iontophoretic delivery devices have been developed in which the donor and counter electrode assemblies have a "multi-laminate" construction. In these devices, the donor and counter electrode assemblies are each formed by multiple layers of (usually) polymeric matrices. For example, Parsi U.S. Pat. No. 4,731,049 discloses a donor electrode assembly having hydrophilic polymer based electrolyte reservoir and drug reservoir layers, a skin-contacting hydrogel layer, and optionally one or more semipermeable membrane layers. Sibalis U.S. Pat. No. 4,640,689 discloses in FIG. 6 an iontophoretic delivery device having a donor electrode assembly comprised of a donor electrode (204), a first drug reservoir (202), a semipermeable membrane layer (200), a second drug reservoir (206), and a microporous skin-contacting membrane (22'). The electrode can be formed of a carbonized plastic, metal foil or other conductive films such as a metalized mylar film. In addition, Ariura et al, U.S. Pat. No. 4,474,570 discloses a device wherein the electrode assemblies include a conductive resin film electrode layer, a hydrophilic gel reservoir layer, a current distribution and conducting layer and an insulating backing layer. Ariura et al disclose several different types of electrode layers including an aluminum foil electrode, a carbon fiber nonwoven fabric electrode and a carbon-containing rubber film electrode.

Others have suggested using biomedical electrodes having current distribution members composed of a rubber or other polymer matrix loaded with a conductive filler such as powdered metal. See for example, U.S. Pat. No. 4,367,745. Such films however, have several disadvantages. First, as metal particle loading in a polymer matrix approaches about 65 vol%, the matrix begins to break down and becomes too brittle to be handled. Even at metal particle loadings only about 50 to 60 vol%, the films produced are extremely rigid and do not conform well to non-planar surfaces. This is a particular disadvantage when designing an electrode adapted to be worn on the skin or a mucosal membrane. An iontophoretic electrode adapted to be worn on a body surface must have sufficient flexibility to contour itself to the natural shape of the body surface to which it is applied.

The drug and electrolyte reservoir layers of iontophoretic delivery devices have been formed of hydrophilic polymers. See for example, Ariura et al, U.S. Pat. No. 4,474,570; Webster U.S. Pat. No. 4,383,529 and Sasaki U.S. Pat. No. 4,764,164. There are several reasons for using hydrophilic polymers. First, water is the preferred solvent for ionizing many drug salts. Secondly, hydrophilic polymer components (i.e., the drug reservoir in the donor electrode and the electrolyte reservoir in the counter electrode) can be hydrated while attached to the body by absorbing water from the skin (i.e., through transepidermal water loss or sweat) or from a mucosal membrane (e.g., by absorbing saliva in the case of oral mucosal membranes). Once hydrated, the device begins to deliver ionized agent to the body. This enables the drug reservoir to be manufactured in a dry state, giving the device a longer shelf life.

The prior art has also recognized that certain electrode compositions are preferred from the standpoint of drug delivery efficiency and minimizing skin burns caused by pH extremes. For example, U.S. Pat. Nos. 4,744,787; 4,747,819 and 4,752,285 all disclose iontophoretic electrodes which are either oxidized or reduced during operation of the device. Preferred electrode materials include a silver anodic electrode, which is used to deliver the chloride salt of a drug, and a silver/silver chloride cathodic (return) electrode. Silver ions generated at the anode combine with the drug counter ion (i.e., chloride ions) to produce an insoluble silver chloride precipitate. This reduces competition between the drug ions and the silver ions for delivery into the body and increases the efficiency of the device.

DISCLOSURE OF THE INVENTION

It is an object of this invention to provide an improved electrode for an iontophoretic delivery device.

This and other objects are met by an electrically powered iontophoretic delivery device including a donor electrode assembly, a counter electrode assembly and a source of electrical power adapted to be electrically connected to the donor and counter electrode assemblies. At least one of the donor and counter electrode assemblies includes an agent reservoir containing an agent, the agent reservoir adapted to be placed in agent transmitting relation with a body surface, and an electrode adapted to be electrically connected to the source of electrical power and to the agent reservoir. The electrode comprises a polymeric matrix containing about 5 to 40 vol% of a conductive filler which forms a conductive network through the matrix, and about 5 to 40 vol% of a chemical species which is able to undergo either oxidation or reduction during operation of the device.

When the electrode is an anode, the chemical species is able to undergo oxidation and is preferably a metal such as silver or zinc. When the electrode is a cathode, the chemical species is able to undergo reduction during operation of the device, and is preferably silver chloride. The conductive filler preferably comprises electrically conductive fibers, such as graphite or carbon fibers.

MODES FOR CARRYING OUT THE INVENTION

Figure 1:
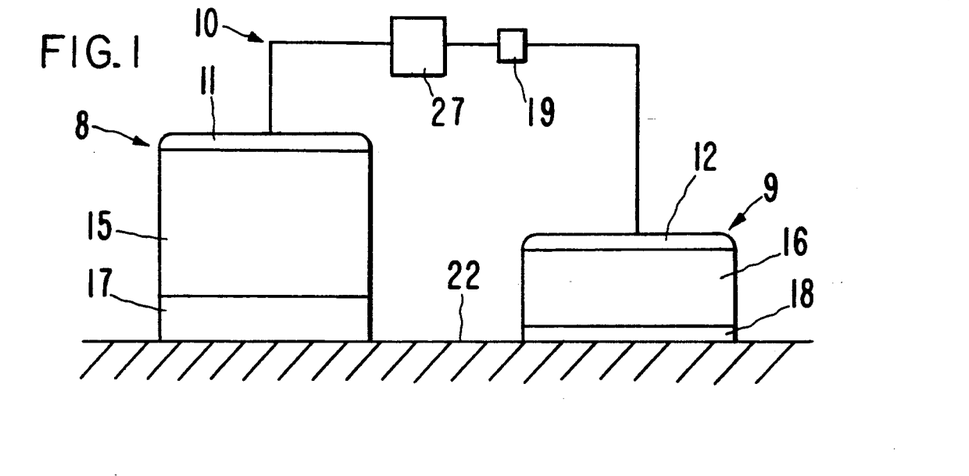
FIG. 1 is a schematic view of an iontophoretic drug delivery device according to the present invention.

FIG. 1 is a schematic view of an iontophoretic delivery device 10 for delivering a beneficial agent through a body surface 22. Body surface 22 is typically intact skin or a mucosal membrane. Iontophoretic delivery device 10 includes a donor electrode assembly 8, a counter electrode assembly 9, an electrical power source 27 (e.g., a battery) and an optional control circuit 19.

The donor electrode assembly 8 includes a donor electrode 11 and an agent reservoir 15. The agent reservoir 15 contains the beneficial agent to be iontophoretically delivered by device 10. The donor electrode assembly 8 is adhered to the body surface 22 by means of an ion-conducting adhesive layer 17.

Iontophoretic delivery device 10 includes a counter electrode assembly 9 which is placed on the body surface 22 at a location spaced apart from electrode assembly 8. Counter electrode assembly 9 includes a counter electrode 12 and an electrolyte reservoir 16. Counter electrode assembly 9 is adhered to the body surface 22 by means of an ion-conducting adhesive layer 18. The donor and counter electrode assemblies 8 and 9 normally include a strippable release liner, not shown, which is removed prior to application of electrode assemblies 8 and 9 to body surface 22. The electrolyte reservoir 16 contains a pharmacologically acceptable salt. Suitable electrolytes for reservoir 16 include sodium chloride, alkaline salts, chlorides, sulfates, nitrates, carbonates, phosphates, and organic salts such as ascorbates, citrates, acetates and mixtures thereof. Reservoir 16 may also contain a buffering agent. Sodium chloride is a suitable electrolyte when the counter electrode 12 is the cathode and is composed of silver/silver chloride, optionally with a sodium phosphate buffer.

When the device 10 is in storage, no current flows because the device forms an open circuit. When the device 10 is placed on the skin or mucosal membrane of a patient, the circuit between the electrodes is closed and the power source begins to deliver current through the device and through the body of the patient. Electrical current flowing through the conductive portions of the device 10 (i.e., those portions used to connect the power source 27 to the electrodes 11 and 12) is carried by electrons (electronic conduction), while current flowing through the hydrated portions of the device 10 (e.g., the agent reservoir 15, the electrolyte reservoir 16 and the ion-conducting adhesive layers 17 and 18) is carried by ions (ionic conduction). In order for current to flow through the device, it is necessary for electrical charge to be transferred from electrodes 11 and 12 to chemical species in solution in reservoirs 15 and 16, respectively, by means of oxidation and reduction charge transfer reactions at the electrodes.

Electrodes 11 and 12 are each comprised of a polymeric matrix containing a conductive filler and a chemical species which is able to undergo either oxidation or reduction during operation of the device. Any polymer which can be suitably mixed with the conductive filler and the chemical species may be used as the polymeric matrix of electrodes 11 and 12. Examples of suitable polymers for use as the matrix of electrodes 11 and 12 include, without limitation, polyalkenes, polyisoprenes, rubbers, polyvinylacetate, ethylene vinyl acetate copolymers, polyamides, polyurethanes, polyvinylchloride, cellulosic polymers, polyethylene oxides, and polyacrylic acid polymers. A preferred polymeric matrix for electrodes 11 and 12 is a copolymer of ethylene vinyl acetate.

The polymeric matrix of electrodes 11 and 12 should contain about 5 to 40 vol%, preferably about 15 to 30 vol%, and most preferably about 20 to 25 vol% of a conductive filler which forms a conductive network through the polymeric matrix. The conductive filler forming the conductive network in the polymeric matrix is preferably comprised of carbon or graphite fibers.

The matrix also contains about 5 to 40 vol%, preferably about 15 to 30 vol%, and most preferably about 20 to 25 vol% of a chemical species which is able to undergo either oxidation or reduction during operation of the device. As mentioned above, as electrical current flows through device 10, oxidation or reduction of some chemical species takes place along the surface of at least one of the electrodes 11 and 12. Although a variety of electrochemical reactions can be utilized, the present invention utilizes a class of charge transfer reactions whereby a portion of at least one of the electrodes 11 and 12 participates in a charge transferring chemical reaction, i.e., a material in at least one of the electrodes 11 and 12 is consumed or generated. This is accomplished through oxidation and/or reduction reactions occurring at the electrodes. Examples of preferred oxidation/reduction reactions include the following:

$$Ag \rightleftharpoons Ag^+ + e^-$$

$$Zn \rightleftharpoons Zn^{+2} + 2e^-$$

$$Cu \rightleftharpoons Cu^{+2} + 2e^-$$

$$Ag + Cl^- \rightleftharpoons AgCl + e^-$$

$$Zn + 2Cl^- \rightleftharpoons ZnCl_2 + 2e^-$$

where the forward reaction is the oxidation reaction taking place at the anodic electrode and the reverse reaction is the reduction reaction taking place at the cathodic electrode. Other standard electrochemical reactions and their respective reduction potentials are well known in the art. See the CRC Handbook of Chemistry and Physics. pp D 151–58, 67th edition (1986–1987).

If the electrode is to be used as an anode, the chemical species should be able to undergo oxidation during operation of the device. Suitable chemical species able to undergo oxidation include metals such as silver, zinc, copper, nickel, tin, lead, iron, chromium and other oxidizable species listed in the CRC Handbook of Chemistry and Physics. 57th edition, D-141 to D-146. Preferred chemical species able to undergo oxidation are metals, preferably in the form of powders. Most preferred are silver and zinc powders.

If the electrode is to be used as a cathode, the chemical species should be able to undergo reduction during operation of the device. Suitable chemical species which are able to undergo reduction include silver chloride, silver bromide, silver hexacyanoferrate, and other reducible species listed in the CRC Handbook of Chemistry and Physics. 57th edition, D-141 to D-146. Of these, silver chloride is most preferred.

It is possible to combine the functions of the conductive filler and the oxidizable/reducible chemical species in a single material. For example, metal coated graphite fibers provide both the conductive network and the chemical species able to undergo oxidation.

Figure 3:
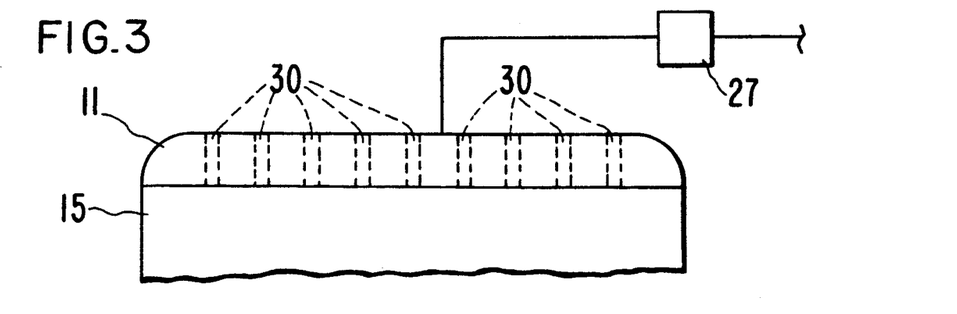
FIG. 3 is a side sectional view of one embodiment of an iontophoretic electrode.

In one alternate embodiment shown in FIG. 3, electrode 11 has a plurality of fluid flow pathways 30 running therethrough. Pathways 30 can be formed by any number of known means such as by punching the electrode 11 after it is made or by forming the pathways at the time the electrode is made (e.g., by molding) using a mold insert. Alternatively, the pathways 30 in electrode 11 (or electrode 12) can be formed by mixing a sufficient quantity, generally about 10 to 50 vol%, preferably about 20 to 35 agent throughout the matrix of electrode 11. In all of these cases, a plurality of pathways through the electrode 11 are formed which can carry a solvent, such as water, therethrough. The electrode of FIG. 3 has an additional advantage in that it permits the delivery device, and specifically the agent reservoir, to be manufactured in a non-hydrated condition, thereby giving the device a longer and more stable shelf life. Water, and/or another liquid solvent, can be applied to the electrode surface at the time of use. The pore forming agent sorbs solvent (e.g., water) thereby allowing water transport along a plurality of fluid flow pathways 30 through the "porous" electrode matrix to hydrate the underlying drug or electrolyte reservoir layer and place the device in an operational (i.e., hydrated) condition.

The pore-formers useful for forming the pathways 30 in electrodes 11 and 12 include solids and pore-forming liquids. The expression pore-forming liquids generically embraces semi-solids and viscous fluids. The term pore-former for both solids and liquids includes substances that can be dissolved, extracted or leached from the electrode by a fluid, preferably water, to form an open-cell type porous structure. Additionally, the pore-formers suitable for the invention include pore-formers that can be dissolved, leached, or extracted without causing physical or chemical changes in the electrode polymer matrix. The pore-forming solids generally have a size of about 0.1 to 200 microns and they include alkali metal salts such as lithium carbonate, sodium chloride, sodium bromide, sodium carbonate, potassium chloride, potassium sulfate, potassium phosphate, sodium benzoate, sodium acetate, sodium citrate, potassium nitrite, and the like; the alkaline earth metal salts such as calcium phosphate, calcium nitrate, calcium chloride, and the like; the transition metal salts such as ferric chloride, ferrous sulfate, zinc sulfate, cupric chloride, manganese fluoride, manganese fluorosilicate, and the like; organic compounds such as polysaccharides including the sugars sucrose, glucose, fructose, mannitol, mannose, galactose, aldohexose, altrose, talose, sorbitol and the like. The pore formers can also be soluble polymers such as starch-graft poly(Na acrylate co-acrylamide) polymers, Carbowaxes ®, Carbopol ®, and the like. Preferred pore formers are starch-graft poly (Na-acrylate co-acrylamide) polymers sold under the tradename Waterlock ® by Grain Processing Corp., Muscatine, Iowa. The pore-formers are non-toxic and form fluid flow pathways 30 through the electrode matrix. The pathways 30 are effective to convey water and/or other liquid solvent to the underlying drug or electrolyte reservoir, enabling the underlying reservoir to be quickly hydrated using an external source of liquid solvent (e.g., water) for quick start-up of the device.

Figure 2:
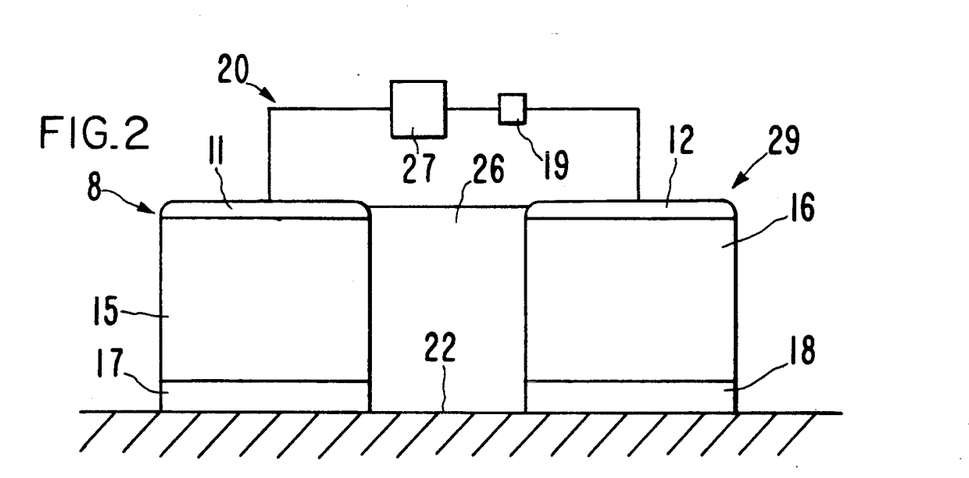
FIG. 2 is a schematic view of another embodiment of an iontophoretic delivery device according to the present invention.

FIG. 2 illustrates another iontophoretic delivery device designated by the numeral 20. Like device 10, device 20 also contains an electrical power source 27 (e.g., a battery) and an optional control circuit 19. However, in device 20 the donor electrode assembly 8 and the counter electrode assembly 9 are physically attached to insulator 26 and form a single self-contained unit. Insulator 26 prevents the electrode assemblies 8 and 9 from short circuiting by preventing electrical and/or ion transport between the electrode assemblies 8 and 9. Insulator 26 is preferably formed of a hydrophobic non-conducting polymeric material which is impermeable to both the passage of ions and water. A preferred insulating material is a nonporous ethylene vinyl acetate copolymer.

Alternatively, both the donor electrode assembly 8 and the counter electrode assembly 9 may be used to iontophoretically deliver different beneficial agents through body surface 22. For example, positive agent ions can be delivered through body surface 22 from the anodic electrode assembly, while negative agent ions can be delivered from the cathodic electrode assembly. Alternatively, neutral drugs can be introduced from either electrode assembly by electroosmosis.

As an alternative to the side-by-side alignment of the donor electrode assembly 8, the insulator 26 and the counter electrode assembly 9 shown in FIG. 2, the electrode assemblies can be concentrically aligned with the counter electrode assembly positioned centrally and surrounded by the insulator 26 and the donor electrode assembly. The electrode assemblies can, if desired, be reversed with the counter electrode assembly surrounding the centrally positioned donor electrode assembly. The concentric alignment of the electrode assemblies can be circular, elliptical, rectangular or any of a variety of geometric configurations.

Power source 27 is typically one or more batteries. As an alternative to a battery, device 10 can be powered by a galvanic couple formed by the donor electrode 11 and counter electrode 12 being composed of dissimilar electrochemical couples and being placed in electrical contact with one other. Typical materials for delivering a cationic agent into the body include a zinc donor electrode 11 and a silver/silver chloride counter electrode 12. A Zn-Ag/AgCl galvanic couple provides an electrical potential of about 1 volt.

The agent and electrolyte reservoirs 15 and 16 can be formed by blending the desired agent, drug, electrolyte or other component(s), with the polymer by melt blending, solvent casting or extrusion, for example. The drug and/or electrolyte loading in the polymer matrix is generally about 10 to 60 wt%, although drug and/or electrolyte loadings outside this range may also be used.

Suitable polymers for use as the matrix of reservoirs 15 and 16 include, without limitation, hydrophobic polymers such as polyethylene, polypropylene, polyisoprenes and polyalkenes, rubbers, copolymers such as Kraton®, polyvinylacetate, ethylene vinyl acetate copolymers, polyamides including nylons, polyurethanes, polyvinylchloride, cellulose acetate, cellulose acetate butyrate, ethylcellulose, cellulose acetate, and blends thereof; and hydrophilic polymers such as hydrogels, polyethylene oxides, Polyox®, Polyox® blended with polyacrylic acid or Carbopol®, cellulose derivatives such as hydroxypropyl methyl cellulose, hydroxyethyl cellulose, hydroxypropyl cellulose, pectin, starch, guar gum, locust bean gum, and the like, along with blends thereof.

The adhesive properties of the reservoirs 15 and 16 may be enhanced by adding a resinous tackifier. This is especially important when using a non-tacky polymeric matrix. Examples of suitable tackifiers include products sold under the trademarks Staybelite Ester #5 and #10, Regal-Rez and Piccotac, all of Hercules, Inc. of Wilmington, Del. Additionally, the matrix may contain a rheological agent, suitable examples of which include mineral oil and silica.

In addition to the drug and electrolyte, the reservoirs 15 and 16 may also contain other conventional materials such as dyes, pigments, inert fillers, and other excipients.

A control circuit 19 is optionally provided. Control circuit 19 may take the form of an on-off switch for "on-demand" drug delivery (e.g., on-demand delivery of an analgesic for pain control), a timer, a fixed or variable electrical resistor, a controller which automatically turns the device on and off at some desired periodicity to match the natural or circadian patterns of the body, or other more sophisticated electronic control devices known in the art. For example, it may be desirable to deliver a predetermined constant level of current from device 10 since a constant current level ensures that the drug or agent is delivered through the skin at a constant rate. The current level can be controlled by a variety of known means, for example, a resistor or a field effect transistor or a current limiting diode. Control circuit 19 may also include a microchip which could be programmed to control the dosage of beneficial agent, or even to respond to sensor signals in order to regulate the dosage to maintain a predetermined dosage regimen. A relatively simple controller or microprocessor can control the current as a function of time, and if desired, generate complex current waveforms such as pulses or sinusoidal waves. In addition, the control circuit 19 may employ a bio-feedback system which monitors a biosignal, provides an assessment of the therapy, and adjusts the drug delivery accordingly. A typical example is the monitoring of the blood sugar level for controlled administration of insulin to a diabetic patient.

As used herein, the expression "agent" can mean a drug or other beneficial therapeutic agent when referring to the donor electrode assembly and/or an electrolyte salt when referring to the counter electrode assembly. The expressions "drug" and "therapeutic agent" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, psychostimulants, sedatives and tranquilizers.

The invention is also useful in the controlled delivery or peptides, polypeptides, proteins and other macromolecules. These macromolecular substances typically have a molecular weight of at least about 300 daltons, and more typically a molecular weight in the range of about 300 to 40,000 daltons. Specific examples of peptides and proteins in this size range include, without limitation, LHRH, LHRH analogs such as buserelin, gonadorelin, naphrelin and leuprolide, GHRH, insulin, heparin, calcitonin, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc.), follicle luteoids, $\alpha$ANF, growth factor releasing factor (GFRF), $\beta$MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hyaluronidase, interferon, interleukin-2, menotropins (urofollitropin (FSH) and LH), oxytocin, streptokinase, tissue plasminogen activator, urokinase, vasopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 anti-trypsin (recombinant). It is most preferable to use a water soluble salt of the drug or agent to be delivered.

The combined skin-contacting areas of electrode assemblies 8 and 9 can vary from less than 1 cm$^2$ to greater than 200 cm$^2$. The average device 10 however, will have electrode assemblies with a combined skin-contacting area within the range of about 5–50 cm$^2$.

As an alternative to the ion-conducting adhesive layers 17 and 18 shown in FIGS. 1 and 2, the iontophoretic delivery devices 10 and 20 may be adhered to the skin using an adhesive overlay. Any of the conventional adhesive overlays used to secure passive transdermal delivery devices to the skin may be used. Another alternative to the ion-conducting adhesive layers 17 and 18 is a peripheral adhesive layer surrounding reservoir 15 and/or 16, allowing reservoir 15 and/or 16 to have a surface in direct contact with the patient's skin.

Having thus generally described our invention, the following examples will illustrate preferred embodiments thereof.

EXAMPLE I

An anodic electrode was made by mixing powdered zinc and graphite fibers into an ethylene vinyl acetate copolymer matrix. First, 23.5 g of ethylene vinyl acetate copolymer having a vinyl acetate content of 9% (EVA 9) were added to a 50 cm$^3$ Brabender mixer (Brabender Instruments, Inc., South Hackensack, N.J.). The mixer bowl was preheated to 90° C. and the blade speed was set at 30 rpm. The EVA 9 polymer was mixed for about five minutes until all of the pellets had been fused. Thereafter, 20.3 g of graphite fibers having a diameter of 8 microns and a length of 6.4 mm was slowly added into the mixer over a period of about five minutes. Thereafter, 80.3 g of zinc powder having an average particle size of about 8 microns was slowly added to the mixer over a period of about five minutes. Thereafter, the blade speed was increased to 40 rpm for an additional 20 minutes of mixing.

Five batches of the material (about 250 cm$^3$) were then loaded into a Brabender extruder having a 0.75 inch screw. The temperature at the screw was about 110° C. An adjustable sheet extrusion die having a die opening with a width of 4 inches and a height adjustable between 1 and 40 mils was mounted at the end of the extruder. The temperature of the film at the die opening was 130° C. After extrusion, the film was passed between opposing calender rolls heated to about 160° C. The calendered film had a thickness of 6 mils.

The film exhibited a voltage drop of less than 0.5 volts when a current density of 100 $\mu$A/cm$^2$ of direct current was passed through the film.

Experiments were conducted to evaluate the electrochemical performance of the anodic film electrode in comparison with the electrochemical performance of an electrode composed of pure zinc. The apparatus used to measure the electrochemical performance of the electrodes included a cell containing an electrolyte solution and means for connecting an anode and a cathode within the cell. The electrodes of the cell are connected in series with a potentiostat which is set to supply the necessary voltage to maintain a constant current level of 100 $\mu$A/cm$^2$ through the circuit. Normal saline was used as the liquid electrolyte solution in the cell. The cell voltage required to pass 100 $\mu$A/cm$^2$ of current was monitored as a function of time for a period of 24 hours.

A control experiment used pure zinc as the anode, a silver chloride cathode and the saline electrolyte. The cell voltage was monitored and recorded over a 24 hour test period. A duplicate experiment was run with the Zn/C fiber/EVA 9 anodic film electrode. The cathodic electrode in both the control and actual experiments was composed of AgCl. Over the entire 24 hour test period, the measured cell voltage of the anodic film electrode was less than 0.3 volts greater than the measured cell voltage of the pure zinc electrode. This small increase in the measured cell voltage is considered to be acceptable for an electrode used in a transdermal iontophoretic delivery device. In general, electrode materials requiring the least amount of additional voltage to deliver the required amount of electrical current are most preferred. Accordingly, the anodic film electrode of the present invention exhibits an electrochemical performance that is only marginally below the performance of a pure zinc anodic electrode.

EXAMPLE II

A cathodic electrode was made by mixing silver chloride powder and graphite fibers into an ethylene vinyl acetate copolymer matrix. First, 23.5 g of ethylene vinyl acetate copolymer having a vinyl acetate content of 9% (EVA 9) were added to a 50 cm$^3$ Brabender mixer. The mixer bowl was preheated to 90° C. and the blade speed was set at 30 rpm. The polymer EVA 9 was mixed for about five minutes until all of the pellets had been fused. Thereafter, 20.3 g of graphite fibers having a diameter of 8 microns and a length of 6.4 mm were slowly added into the mixer over a period of about five minutes.

Thereafter, 62.6 g of granular silver chloride having a particle size of less than 100 microns was slowly added to the mixer over a period of about five minutes. Thereafter, the blade speed was increased to 40 rpm for an additional 20 minutes of mixing.

Five batches of the material (about 250 cm$^3$) were then loaded into the same extruder/die combination described in Example I. The temperature at the screw was about 105° C. The temperature of the film at the die opening was about 130° C. After extrusion, the film was passed between opposing calender rolls heated to about 160° C. The calendered film had a thickness of 6 mils.

The cathodic film exhibited a voltage drop of less than 0.5 volts when a current density of 100 $\mu$A/cm$^2$ of direct current was passed through the film.

Experiments were conducted to evaluate the electrochemical performance of the AgCl/C fiber/EVA 9 cathodic film electrode in comparison with the electrochemical performance of an electrode composed of silver chloride, using the same apparatus and procedures described in Example I. The anodic electrode in both the control and actual experiments was composed of pure zinc. Over the entire 24 hour test period, the measured cell voltage of the cathodic film electrode was less than 0.3 volts greater than the measured cell voltage of the silver chloride electrode. This small increase in the measured cell voltage is considered to be acceptable for an electrode used in a transdermal iontophoretic delivery device. In general, electrode materials requiring the least amount of additional voltage to deliver the required amount of electrical current are most preferred. Accordingly, the cathodic film electrode of the present invention exhibits an electrochemical performance that is only marginally below the performance of a silver chloride cathodic electrode.

Having thus generally described our invention and described in detail certain preferred embodiments thereof, it will be readily apparent that various modifications to the invention may be made by workers skilled in the art without departing from the scope of this invention and which is limited only by the following claims.

What is claimed is:

1. An electrically powered iontophoretic delivery device including a donor electrode assembly, a counter electrode assembly and a source of electrical power adapted to be electrically connected to the donor electrode assembly and the counter electrode assembly, at least one of the electrode assemblies including an agent reservoir containing an agent, the agent reservoir adapted to be placed in agent transmitting relation with a body surface, and an electrode adapted to be electrically connected to the source of electrical power and to the agent reservoir, wherein the electrode comprises:
   a polymeric matrix;
   about 5 to 40% of a conductive filler forming a conductive network through the matrix; and
   about 5 to 40 vol% of a chemical species able to undergo oxidation or reduction during operation of the device, the matrix having a plurality of fluid flow pathways therethrough.

2. The device of claim 1, wherein the electrode is an anode and the chemical species is a metal able to undergo oxidation during operation of the device.

3. The device of claim 2, wherein the metal is selected from the group consisting of silver and zinc.

4. The device of claim 1, wherein the electrode is a cathode and the chemical species is able to undergo reduction during operation of the device.

5. The device of claim 4, wherein the chemical species able to undergo reduction is selected from the group consisting of AgCl, AgBr, and Ag$_4$Fe(CN)$_6$.

6. The device of claim 1, wherein the conductive filler comprises carbon fibers.

7. The device of claim 1, wherein the polymer comprises a hydrophobic polymer.

8. The device of claim 7, wherein the hydrophobic polymer is selected from the group consisting of ethylene vinyl acetate copolymers, polyalkylenes, polyisoprenes, rubbers, polyvinylacetate, polyamides, polyurethanes, polyvinylchlorides, and modified cellulosic polymers.

9. The device of claim 1, wherein the matrix is in the form of a film.

10. The device of claim 9, wherein the conductive filler comprises carbon fibers, the carbon fibers forming an unoriented conductive carbon fiber network within the film.

11. The device of claim 1, wherein the fluid flow pathways are comprised of a pore forming agent in the polymeric matrix.

12. The device of claim 1, wherein the counter electrode assembly includes a counter electrode adapted to be electrically connected to the source of electrical power and an electrolyte reservoir adapted to be placed in electrolyte transmitting relation with the body surface the counter electrode being in electrical contact with the electrolyte reservoir; wherein the counter electrode comprises:
   a polymeric matrix;
   about 5 to 40 vol% of a conductive filler forming a conductive network through the matrix; and
   about 5 to 40 vol% of a chemical species able to undergo oxidation or reduction during operation of the device.

13. The device of claim 12, wherein the electrolyte reservoir is a polymeric matrix comprised of about 10 to 60 wt% of a hydrophilic polymer about 10 to 60 wt% of a hydrophobic polymer and up to about 50 wt% of the electrolyte.

14. The device of claim 1, wherein the donor electrode assembly includes a donor electrode adapted to be electrically connected to the source of electrical power and a drug reservoir adapted to be placed in drug transmitting relation with the body surface the donor electrode having a surface which is in contact with the drug reservoir.

15. The device of claim 14, wherein the drug reservoir is a polymeric matrix comprised of about 10 to 60 wt% of a hydrophilic polymer, about 10 to 60 wt% of a hydrophobic polymer and up to about 50 wt% of the drug.

16. The device of claim 1, wherein the power source comprises a battery.

17. The device of claim 1, wherein the agent comprises a drug.

18. The device of claim 17, wherein the drug is a water soluble drug salt.

19. The device of claim 1, wherein the agent comprises an electrolyte.

20. The device of claim 19, wherein the electrolyte comprises a water soluble electrolyte salt.

21. The device of claim 12, wherein a plurality of fluid flow pathways are provided through the counter electrode.

22. The device of claim 21, wherein the fluid flow pathways are comprised of a pore forming agent in the polymeric matrix.

23. The device of claim 11 or 22, wherein the matrix contains about 10 to 50 vol% of the pore forming agent.

24. The device of claim 11 or 22, wherein the matrix contains about 20 to 35 vol% of the pore forming agent.

25. The device of claim 11 or 22, wherein the pore forming agent is selected from the group consisting of pore forming solids and pore forming liquids.

26. The device of claim 11 or 22, wherein the pore forming agent comprises a material which sorbs water.

27. The device of claim 11 or 22, wherein the pore forming agent comprises a material which is dissolved, extracted or leached by water.

28. The device of claim 11 or 22, wherein the pore forming agent comprises a polymer which sorbs water.

29. The device of claim 28, wherein the pore forming agent is a polymer which is water soluble.

30. The device of claim 29, wherein the pore forming agent is a polymer which is water swellable.

31. The device of claim 11 or 22, wherein the pore forming agent comprises a salt.

32. The device of claim 11 or 22, wherein the pore forming agent is a polymer selected from the group consisting of starch-graft poly (Na-acrylate co-acrylamide) polymers and polyethylene oxides.

33. The device of claim 11 or 22, wherein the pore forming agent comprises a polysaccharide.

34. A method of activating a non-hydrated electrode assembly in an electrically powered iontophoretic delivery device, the device including a donor electrode assembly, a counter electrode assembly and a source of electrical power adapted to be electrically connected to the donor electrode assembly and the counter electrode assembly, at least one of the electrode assemblies including a non-hydrated agent reservoir containing an agent and an electrode, comprising:

electrically connecting the electrode, which electrode is comprised of a polymeric matrix, about 5 to 40 vol% of a conductive filler forming a conductive network through the matrix and about 5 to 40 vol% of a chemical species able to undergo oxidation or reduction during operation of the device, to the source of electrical power and to the agent reservoir;

forming a plurality of fluid flow pathways through the polymer matrix of the electrode;

delivering a liquid solvent through the plurality of fluid flow pathways into the non-hydrated agent reservoir; and placing the agent reservoir in agent transmitting relation with a body surface.

35. The method of claim 34, wherein the step of forming the plurality of fluid flow pathways comprises mixing a pore forming agent into the polymer matrix.

36. The method of claim 34, wherein the fluid flow pathways are formed by punching the pathways through the electrode.

37. The method of claim 34, wherein the fluid flow pathways are formed by molding the pathways through the electrode.

38. The method of claim 35, wherein the pore forming agent is selected from the group consisting of pore forming solids and pore forming liquids.

39. The method of claim 35, wherein the pore forming agent sorbs water.

40. The method of claim 35, wherein the pore forming agent is dissolved, extracted or leached by water.

41. The method of claim 35, wherein the pore forming agent comprises a polymer which sorbs water.

42. The method of claim 35, wherein the pore forming agent is a polymer which is water soluble.

43. The method of claim 35, wherein the pore forming agent is a polymer which is water swellable.

44. The method of claim 35, wherein the pore forming agent comprises a salt.

45. The method of claim 35, wherein the pore forming agent is a polymer selected from the group consisting of starch-graft poly (Na-acrylate co-acrylamide) polymers and polyethylene oxides.

46. The method of claim 35, wherein the pore forming agent comprises a polysaccharide.

* * * * *

UNITED STATES PATENT AND TRADEMARK OFFICE
CERTIFICATE OF CORRECTION

PATENT NO. : 5,147,297

DATED : September 15, 1992

INVENTOR(S) : Robert M. Myers and Mark G. Stahl

It is certified that error appears in the above-identified patent and that said Letters Patent is hereby corrected as shown below:

Column 11, line 58, after "40", insert --vol--.

Signed and Sealed this

Twenty-eighth Day of September, 1993

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,147,297
DATED : September 15, 1992
INVENTOR(S) : MYERS, et al.

It is certified that error appears in the above-identified patent and that said Letters Patent is hereby corrected as shown below:

In column 6, line 17, following the number "35" insert --vol% and most preferably about 25 to 30 vol%, of a pore forming--.

Signed and Sealed this

Twenty-second Day of March, 1994

Attest:

BRUCE LEHMAN

Attesting Officer    Commissioner of Patents and Trademarks